Sept. 3, 1974 B. J. MACHIN Plant Pat. 3,607
CHRYSANTHEMUM PLANT
Filed April 12, 1973
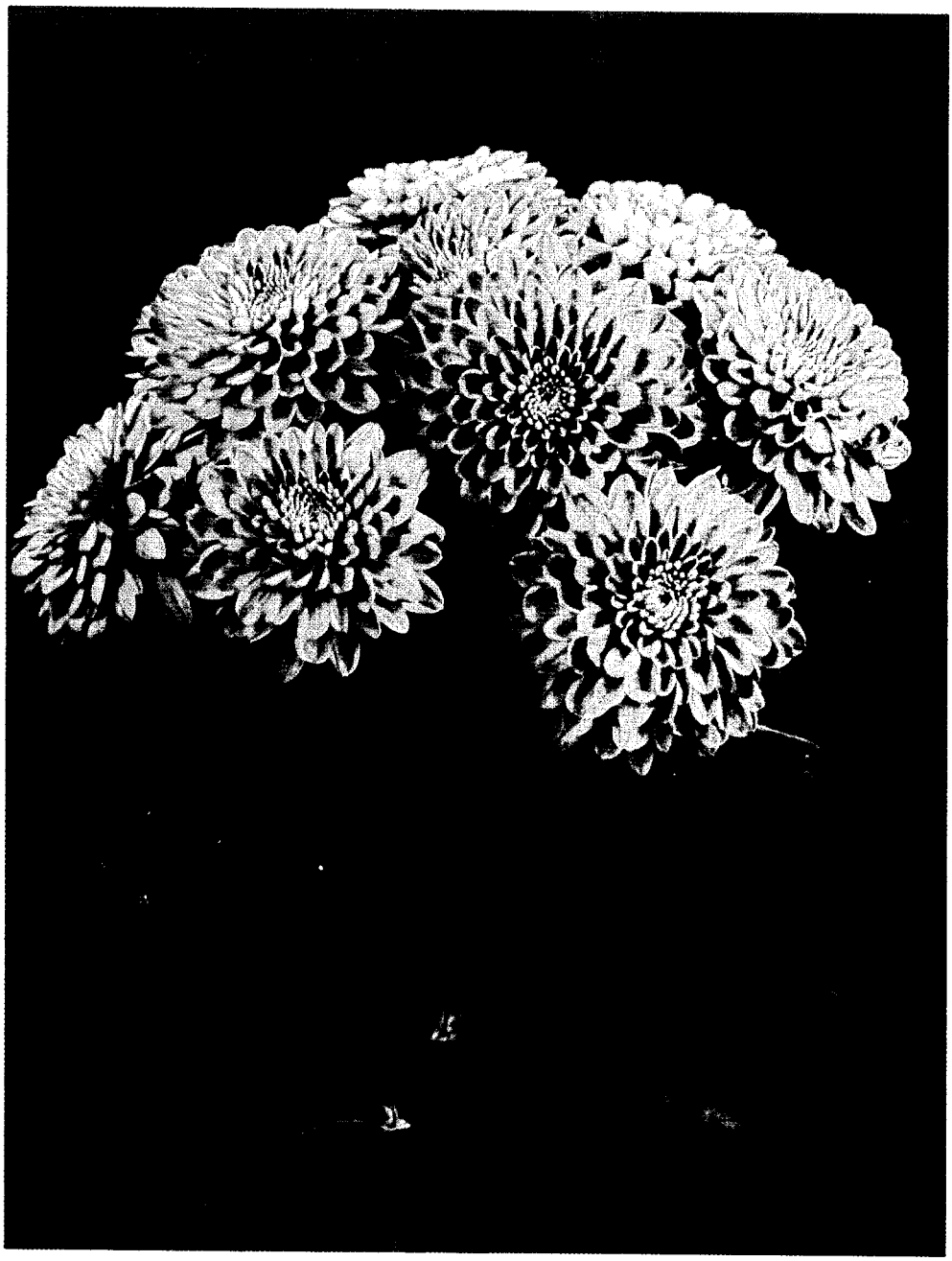

United States Patent Office

Plant Pat. 3,607

Patented Sept. 3, 1974

3,607

CHRYSANTHEMUM PLANT

Barrie John Machin, Chichester, England, assignor to Frampton's Nurseries Limited, Chichester, Sussex, England Filed Apr. 12, 1973, Ser. No. 350,626
Int. Cl. A01h 5/00
U.S. Cl. Plt.—81 1 Claim This invention relates to a new and distinctive variety of *Chrysanthemum morifolium* Bailey (Pot type) known as Deep Popsie.

The new variety Deep Popsie is a sport from a variety known as Popsie which was originated by me from a cross made in 1966 between the variety BGA Bluebell and the variety Apricot Princess Anne, the former being the seed parent and the latter being the pollen parent. The new variety Deep Popsie was induced by irradiation from Popsie in July 1970.

The variety Popsie resulted from an extensive breeding program with the object of producing improved varieties for year round pot chrysanthemum production with particular emphasis on the need for improved varieties which can be used not only for the normal technique of production (4 or 5 cuttings in each pot) but also as single plant specimens in small pots.

The variety Popsie has the following improved characteristics over existing varieties 1. It has an improved breaking action following a pinch so that a flowering shoot is produced from the majority of the leaf axils.
2. It has good and uniform flowering whether or not the apical flower on each shoot is disbudded.
3. The keeping quality of flowers is better.
4. The relatively small pompon-like flowers are hard and crisp and withstand adverse marketing conditions better than most existing varieties.
5. The habit of the plant is more ideal for the production of small pots using single plants.

The variety Deep Popsie is similar to the variety Popsie in the above characteristics but the color is improved since it is deeper, more intense, and fades less in high temperature and/or under low light conditions.

The accompanying drawing shows a typical flower of my new variety depicted in color as nearly true as it is reasonably possible to make the same in a color illustration of this character.

Asexual reproduction of this new variety Deep Popsie by rooting vegetative shoots in Sussex, England shows that the above characteristics are fixed and come true to type through succeeding generations.

The following is a detailed descripion of the new variety Deep Popsie with color terminology in accordance with the Royal Horticultural Society color chart (RHS).

Genus: Chrysanthemum.
Species: Morifolium Bailey.
Type: Pot.
Class: Pompon (or small incurving decorative).
Breeding: The original variety Popsie resulted from a cross between the variety BGA Bluebell and the variety Apricot Princess Anne, the former being the seed parent and the latter the pollen parent. The cross was made in 1966 at Framptons Nurseries, Forbridge Nursery, Cchichester, Sussex, Egnland. The variety Deep Popsie was induced by irradiation from the variety Popsie in July 1970.
Propagation: Holds its distinguishing characteristics through succeeding propagations by rooting vegetative shoots.
Flower: When grown and observed in Sussex, England, as single plants in 3½ in. pots, pinching induces the formation of up to 10 flowering shoots. When produced as a 5½ in. pot plant using 5 cuttings per pot, each plant produces 3 to 6 flowering shoots following a pinch.
Bloom:
*Size.*—Average diameter is 7 cm. when fully open.
*Petalage.*—Approximately 350 ray petals and 10 disc petals.
*Form.*—A small incurving decorative or pompon.
*Petals.*—Short, broad, boat-shaped, thick and of very firm texture.
Color of open bloom:

| | |
|---|---|
| Inner face of fully expanded petal | RHS 74D |
| Outer face of fully expanded petal | RHS 75D |
| Inner face of young petal | RHS 74C |
| Outer face of young petal | RHS 75C |

Response group: 10 weeks.
Temperature tolerance: 57°–60° F. at night.
Plant: Short, stocky and free branching—very suitable for single plant type.
Foliage: Medium size and light green—Color RHS 138A.
Stem: Thick and strong—Color RHS 139D.

I claim:

1. A new and distinct variety of *Chrysanthemum morifolium* Bailey, substantially as shown and described, having an improved breaking action following a pinch and uniform flowering regardless of whether the apical flower on each shoot is disbudded, and characterized particularly as to its novelty by the unique combination of the deep, intense red purple color of its small, hard and crisp flowers which color is resistant to fading under high temperature or low light conditions.

No references cited.

ROBERT E. BAGWILL, Primary Examiner